(12) United States Patent
Austen et al.

(10) Patent No.: US 10,278,677 B2
(45) Date of Patent: May 7, 2019

(54) APPARATUS AND METHOD FOR TISSUE BIOPSY

(75) Inventors: William G. Austen, Weston, MA (US); Dieter Manstein, Coral Gables, FL (US)

(73) Assignee: The General Hospital Corporation, Boston, MA (US)

( * ) Notice: Subject to any disclaimer, the term of this patent is extended or adjusted under 35 U.S.C. 154(b) by 404 days.

(21) Appl. No.: 13/982,085

(22) PCT Filed: Jan. 27, 2012

(86) PCT No.: PCT/US2012/022980
§ 371 (c)(1),
(2), (4) Date: Mar. 26, 2014

(87) PCT Pub. No.: WO2012/103483
PCT Pub. Date: Aug. 2, 2012

(65) Prior Publication Data
US 2014/0200484 A1     Jul. 17, 2014

Related U.S. Application Data

(60) Provisional application No. 61/437,493, filed on Jan. 28, 2011.

(51) Int. Cl.
*A61B 10/00* (2006.01)
*A61B 10/02* (2006.01)
(Continued)

(52) U.S. Cl.
CPC ...... *A61B 10/0266* (2013.01); *A61B 10/0233* (2013.01); *A61B 10/0275* (2013.01);
(Continued)

(58) Field of Classification Search
CPC ............ A61B 10/0233; A61B 10/0266; A61B 10/0275; A61B 17/32053;
(Continued)

(56) References Cited

U.S. PATENT DOCUMENTS 3,001,522 A   9/1961 Silverman
3,683,892 A   8/1972 Harris
(Continued)

FOREIGN PATENT DOCUMENTS

CA        2361777 A1    5/2002
CN      201005966 Y    1/2008
(Continued)

OTHER PUBLICATIONS

International Search Report for International Patent Application No. PCT/US2012/022980 dated Aug. 9, 2012.
(Continued)

*Primary Examiner* — Devin B Henson
(74) *Attorney, Agent, or Firm* — Quarles & Brady LLP

(57) ABSTRACT

Exemplary embodiments of an apparatus can be provided for obtaining portions or samples of tissue from a target region of a biological tissue. One or more needles can be provided that have a small internal diameter, e.g., about 1 mm or less, and the needles can be configured to extract the tissue portions when the needles are inserted into and withdrawn from the tissue. Windows and/or markings can be provided on the wall of the needles to facilitate access to the sample. The needles can be provided in an enclosure, and an actuator can be provided to direct the needles into the tissue and/or withdraw them. A plurality of tissue portions having known relative locations in the target region can be obtained, and extraction of the tissue portions can be well-tolerated by the tissue as compared with conventional punch biopsies or the like.

8 Claims, 3 Drawing Sheets

(51) Int. Cl.
*A61B 90/30* (2016.01)
*A61B 90/92* (2016.01)
*A61B 90/94* (2016.01)
*A61B 17/3205* (2006.01)

(52) U.S. Cl.
CPC .............. *A61B 90/30* (2016.02); *A61B 90/92* (2016.02); *A61B 90/94* (2016.02); *A61B 10/0096* (2013.01); *A61B 10/025* (2013.01); *A61B 17/32053* (2013.01); *A61B 2010/0208* (2013.01); *A61B 2010/0225* (2013.01)

(58) Field of Classification Search
CPC .... A61B 2010/0208; A61B 2010/0225; A61B 10/0096; A61B 10/025; A61B 2017/00752; A61B 2017/00761; A61M 2037/003; A61M 5/3291; A61M 5/3295; A61M 5/3298
See application file for complete search history.

(56) References Cited

U.S. PATENT DOCUMENTS

| | | | |
|---|---|---|---|
| 3,929,123 | A | 12/1975 | Jamshidi |
| 4,108,096 | A | 8/1978 | Ciecior |
| 4,649,918 | A | 3/1987 | Pegg et al. |
| 4,865,026 | A | 9/1989 | Barrett |
| 4,903,709 | A | 2/1990 | Skinner |
| 5,269,316 | A | 12/1993 | Spitalny |
| 5,458,112 | A | 10/1995 | Weaver |
| 5,615,690 | A * | 4/1997 | Giurtino ............ A61B 10/0266 600/567 |
| 5,749,895 | A | 5/1998 | Sawyer et al. |
| 5,885,211 | A | 3/1999 | Eppstein et al. |
| 5,922,000 | A | 7/1999 | Chodorow |
| 6,022,324 | A | 2/2000 | Skinner |
| 6,211,598 | B1 | 4/2001 | Dhuler et al. |
| 6,241,687 | B1 * | 6/2001 | Voegele ............ A61B 10/0266 600/566 |
| 6,251,097 | B1 | 6/2001 | Kline et al. |
| 6,264,618 | B1 | 7/2001 | Landi et al. |
| 6,432,098 | B1 | 8/2002 | Kline et al. |
| 6,461,369 | B1 | 10/2002 | Kim |
| 6,562,037 | B2 | 5/2003 | Paton et al. |
| 6,669,618 | B2 | 12/2003 | Reising et al. |
| 6,669,694 | B2 | 12/2003 | Shadduck |
| 6,733,496 | B2 | 5/2004 | Sharkey et al. |
| 6,893,388 | B2 | 5/2005 | Reising et al. |
| 6,936,039 | B2 | 8/2005 | Kline et al. |
| 7,073,510 | B2 | 7/2006 | Redmond et al. |
| 7,131,951 | B2 | 11/2006 | Angel |
| 8,128,639 | B2 | 3/2012 | Tippett |
| 3,209,006 | A1 | 6/2012 | Smith et al. |
| 3,246,611 | A1 | 8/2012 | Paithankar et al. |
| 3,435,791 | A1 | 5/2013 | Galun et al. |
| 8,480,592 | B2 * | 7/2013 | Chudzik ............ A61B 10/0275 600/437 |
| 9,439,673 | B2 | 9/2016 | Austen |
| 2002/0169431 | A1 | 11/2002 | Kline et al. |
| 2003/0088220 | A1 | 5/2003 | Molander et al. |
| 2003/0119641 | A1 | 6/2003 | Reising |
| 2003/0158521 | A1 | 8/2003 | Ameri |
| 2003/0233082 | A1 | 12/2003 | Kline et al. |
| 2004/0023771 | A1 | 2/2004 | Reising et al. |
| 2004/0073195 | A1 | 4/2004 | Cucin |
| 2005/0090765 | A1 | 4/2005 | Fisher |
| 2005/0130821 | A1 | 6/2005 | Reising et al. |
| 2005/0165329 | A1 | 7/2005 | Taylor et al. |
| 2005/0209567 | A1 * | 9/2005 | Sibbitt, Jr. ............ A61B 5/1405 604/187 |
| 2005/0215921 | A1 | 9/2005 | Hibner |
| 2005/0215970 | A1 | 9/2005 | Kline et al. |
| 2005/0215971 | A1 | 9/2005 | Roe et al. |
| 2005/0234419 | A1 | 10/2005 | Kline et al. |
| 2005/0245952 | A1 * | 11/2005 | Feller ............... A61B 17/32053 606/170 |
| 2005/0283141 | A1 | 12/2005 | Giovannoli |
| 2006/0064031 | A1 | 3/2006 | Miller |
| 2006/0116605 | A1 * | 6/2006 | Nakao ............... A61B 10/0266 600/566 |
| 2006/0161179 | A1 | 7/2006 | Kachenmeister |
| 2006/0184153 | A1 | 8/2006 | Mark et al. |
| 2006/0259006 | A1 * | 11/2006 | McKay ............... A61B 17/3478 604/506 |
| 2007/0038181 | A1 * | 2/2007 | Melamud ............ A61B 17/3478 604/158 |
| 2007/0060888 | A1 | 3/2007 | Goff et al. |
| 2007/0073217 | A1 | 3/2007 | James |
| 2007/0073327 | A1 | 3/2007 | Giovannoli |
| 2007/0078466 | A1 * | 4/2007 | Bodduluri ........ A61B 17/32053 606/133 |
| 2007/0078473 | A1 | 4/2007 | Bodduluri et al. |
| 2007/0106306 | A1 | 5/2007 | Bodduluri et al. |
| 2007/0156161 | A1 * | 7/2007 | Weadock ............ A61B 10/0275 606/170 |
| 2007/0179455 | A1 * | 8/2007 | Geliebter ............ A61M 5/329 604/272 |
| 2007/0183938 | A1 * | 8/2007 | Booker ............... A61B 10/0096 422/400 |
| 2007/0198000 | A1 | 8/2007 | Miyamoto et al. |
| 2007/0213634 | A1 | 9/2007 | Teague |
| 2007/0239260 | A1 | 10/2007 | Palanker et al. |
| 2007/0249960 | A1 | 10/2007 | Williamson, IV |
| 2007/0270710 | A1 * | 11/2007 | Frass ................. A61B 10/0045 600/567 |
| 2008/0009802 | A1 | 1/2008 | Lambino et al. |
| 2008/0009901 | A1 | 1/2008 | Redmond et al. |
| 2008/0045858 | A1 | 2/2008 | Tessitore et al. |
| 2008/0132979 | A1 | 6/2008 | Gerber |
| 2008/0234602 | A1 * | 9/2008 | Oostman ............ A61B 10/0266 600/564 |
| 2008/0234699 | A1 | 9/2008 | Oostman, Jr. et al. |
| 2008/0300507 | A1 | 12/2008 | Figueredo et al. |
| 2008/0312648 | A1 | 12/2008 | Peterson |
| 2009/0227895 | A1 | 9/2009 | Goldenberg |
| 2009/0312749 | A1 | 12/2009 | Pini et al. |
| 2010/0023003 | A1 | 1/2010 | Mulholland |
| 2010/0082042 | A1 | 4/2010 | Drews |
| 2010/0121307 | A1 | 5/2010 | Lockard et al. |
| 2010/0160822 | A1 | 6/2010 | Parihar et al. |
| 2010/0185116 | A1 | 7/2010 | Al-Mohizea |
| 2010/0330589 | A1 * | 12/2010 | Bahrami ............ A61M 5/1452 435/7.9 |
| 2011/0105949 | A1 | 5/2011 | Wiksell |
| 2011/0245834 | A1 | 10/2011 | Miklosovic |
| 2011/0251602 | A1 | 10/2011 | Anderson et al. |
| 2011/0282238 | A1 | 11/2011 | Houser et al. |
| 2011/0313429 | A1 | 12/2011 | Anderson et al. |
| 2012/0041430 | A1 | 2/2012 | Anderson et al. |
| 2012/0136387 | A1 | 5/2012 | Redmond et al. |
| 2012/0226214 | A1 | 9/2012 | Gurtner et al. |
| 2012/0226306 | A1 | 9/2012 | Jackson et al. |
| 2012/0253333 | A1 | 10/2012 | Garden et al. |
| 2012/0271320 | A1 | 10/2012 | Hall et al. |
| 2013/0045171 | A1 | 2/2013 | Utecht et al. |
| 2014/0200484 | A1 | 7/2014 | Austen et al. |
| 2014/0277055 | A1 | 9/2014 | Austen, Jr. |
| 2014/0296741 | A1 | 10/2014 | Austen |
| 2016/0095592 | A1 | 4/2016 | Levinson et al. |
| 2016/0367280 | A1 | 12/2016 | Austen |

FOREIGN PATENT DOCUMENTS

| | | |
|---|---|---|
| CN | 101208128 A | 6/2008 |
| CN | 101232858 A | 7/2008 |
| CN | 101347346 A | 1/2009 |
| DE | 202004010659 U1 | 10/2004 |
| EA | 9092 B1 | 10/2007 |
| EP | 0027974 A1 | 5/1981 |
| EP | 1224949 A1 | 7/2002 |
| EP | 1396230 A1 | 3/2004 |
| EP | 1278061 B1 | 2/2011 |

(56) References Cited

FOREIGN PATENT DOCUMENTS

| | | |
|---|---|---|
| EP | 2409727 A1 | 1/2012 |
| JP | 2005000642 A | 1/2005 |
| JP | 2005103276 A | 4/2005 |
| JP | 2009219858 A | 10/2009 |
| JP | 2010515469 A | 5/2010 |
| JP | 2010532178 A | 10/2010 |
| KR | 20100135864 A | 12/2010 |
| RU | 2119304 C1 | 9/1998 |
| RU | 11679 U1 | 11/1999 |
| RU | 28328 U1 | 3/2003 |
| RU | 50799 U1 | 1/2006 |
| RU | 2308873 C2 | 10/2007 |
| SU | 1426740 A1 | 9/1988 |
| SU | 1801391 A1 | 8/1990 |
| WO | WO 93/22971 A1 | 11/1993 |
| WO | 9929243 A1 | 6/1999 |
| WO | 0141651 A2 | 6/2001 |
| WO | WO 2006/118804 A1 | 11/2006 |
| WO | 2007011788 A2 | 1/2007 |
| WO | 2007024038 A1 | 3/2007 |
| WO | 2007106170 A2 | 9/2007 |
| WO | 2009072711 A2 | 6/2009 |
| WO | 2009099988 A2 | 8/2009 |
| WO | 2009137288 A2 | 11/2009 |
| WO | 2009146053 A1 | 12/2009 |
| WO | WO 2009/146068 A1 | 12/2009 |
| WO | 2010027188 A2 | 3/2010 |
| WO | 2010080014 A2 | 7/2010 |
| WO | 2010097790 A1 | 9/2010 |
| WO | 2012052986 A2 | 4/2012 |
| WO | 2012103483 A2 | 8/2012 |
| WO | 2012103488 A1 | 8/2012 |
| WO | 2012103492 A1 | 8/2012 |
| WO | 2012119131 A1 | 9/2012 |
| WO | 2012135828 A1 | 10/2012 |
| WO | 2013013196 A1 | 1/2013 |
| WO | 2013013199 A2 | 1/2013 |
| WO | 2014179729 A1 | 11/2014 |
| WO | 2015021434 A2 | 2/2015 |

OTHER PUBLICATIONS

International Written Opinion for International Patent Application No. PCT/US2012/022980 dated Aug. 9, 2012.
Bolyshaya Meditsinskaya Entsiklopediya, M., 1976, vol. 3, p. 184.
Bolyshaya Meditsinskaya Entsiklopediya, M., 1986, vol. 27, p. 480-481.
Spravochik Operatsionnoy I Perevyazochnoy Sestrie, M., <<Meditsina>>, 1985, p. 31.
The Supplemental European Search Report for European Patent Application No. 12738813.0 dated Jun. 12, 2014.
Bedi, et al., the Effects of Pulse Energy Variations on the Dimensions of Microscopic Thermal Treatment Zones in Nonablative Fractional Resurfacing, Lasers in Surgery and Medicine, 2007, 39:145-155.
Cevc, Review—Biologicals & Immunologicals—Drug Delivery Across the Skin, Expert Opinion on Investigational Drugs, 1997, 6(12):1887-1888.
Chang, An Updated Review of Tyrosinase Inhibitors, International Journal of Molecular Sciences, 2009, 10:2440-2475.
Czech, et al., Pressure-Sensitive Adhesives for Medical Applications, INTECH Open Access Publisher, 2011, pp. 309-332.
Dai, et al., Magnetically-Responsive Self Assembled Composites, Chemical Society Reviews, 2010, 39:4057-4066.
De Las Heras Alarcon, et al., Stimuli Responsive Polymers for Biomedical Applications, Chemical Society Reviews, 2005, 34:276-285.
Dini, et al., Grasping Leather Plies by Bernoulli Grippers, CIRP Annals—Manufacturing Technology, 2009, 58:21-24.
Dujardin, et al., In Vivo Assessment of Skin Electroporation Using Square Wave Pulses, Journal of Controlled Release, 2002, 79:219-227.
European Patent Office, Extended European Search Report, Application No. 128147113, dated Feb. 11, 2015.
Fernandes, et al., Micro-Mechanical Fractional Skin Rejuvenation, Plastic and Reconstructive Surgery, 2012, 130 :5S-1): 28.
Fernandes, et al., Micro-Mechanical Fractional Skin Rejuvenation, Plastic and Reconstructive Surgery, 2013, 131:216-223.
Galaev, 'Smart' Polymers in Biotechnology and Medicine, Russian Chemical Reviews, 1995, 64(5):471-489.
Glogau, Aesthetic and Anatomic Analysis of the Aging Skin, Seminars in Cutaneous Medicine and Surgery, 1996, 15(3):134-138.
Hale, et al., Optical Constants of Water in the 200-nm to 200-μm Wavelength Region, Applied Optics, 1973, 12(3):555-563.
Huang, et al., Shape Memory Materials, Materials Today, 2010, 13(7):54-61.
Kakasheva-Mazenkovska, et al., Variations of the Histomorphological Characteristics of Human Skin of Different Body Regions in Subjects of Different Age, Contributions/Macedonian Academy of Sciences and Arts, Section of Biological and Medical Sciences, 2010 32(2):119-128.
Konermann, et al., Ultrasonographically Guided Needle Biopsy of Benign and Malignant Soft Tissue and Bone Tumors, Journal of Ultrasound in Medicine, 2000, 19(7):465-471.
Lien, et al., A Novel Gripper for Limp Materials Based on Lateral Coanda Ejectors, CIRP Annals—Manufacturing Technology, 2008, 57:33-36.
Majid, Microneedling Therapy in Atrophic Facial Scars: An Objective Assessment, Journal of Cutaneous and Aesthetic Surgery, 2009, 2(1):26-30.
Pliquett, et al., A Propagating Heat Wave Model of Skin Electroporation, Journal of Theoretical Biology, 2008, 251:195-201.
Prausnitz, et al., Electroporation of Mammalian Skin: A Mechanism to Enhance Transdermal Drug Delivery, Proc. Natl. Acad. Sci., 1993, 90:10504-10508.
PCT International Search Report and Written Opinion, PCT/US2012/022993, dated May 17, 2012.
PCT International Search Report and Written Opinion, PCT/US2012/047708, dated Oct. 18, 2012.
PCT International Search Report and Written Opinion, PCT/US2012/047716, dated Oct. 25, 2012.
PCT International Search Report and Written Opinion, PCT/US2014/036638, dated Oct. 2, 2014.
PCT International Preliminary Report on Patentability, PCT/US2014/036638, dated Nov. 3, 2015.
PCT International Search Report and Written Opinion, PCT/US2014/050426, dated Feb. 4, 2015.
PCT International Preliminary Report on Patentability, PCT/US2014/050426, dated Feb. 9, 2016.

* cited by examiner

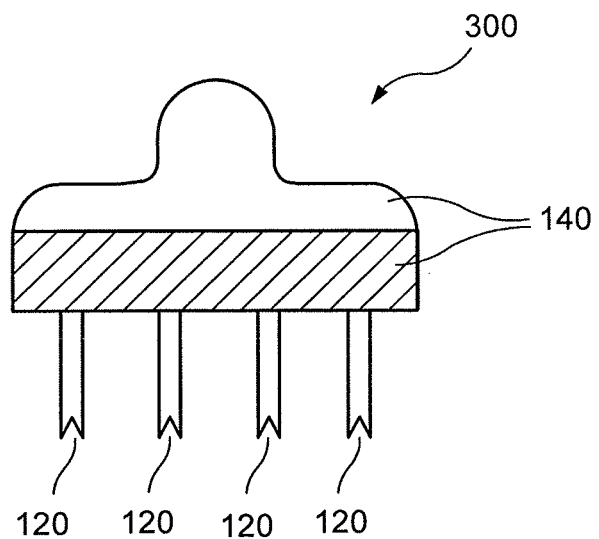
F I G. 3
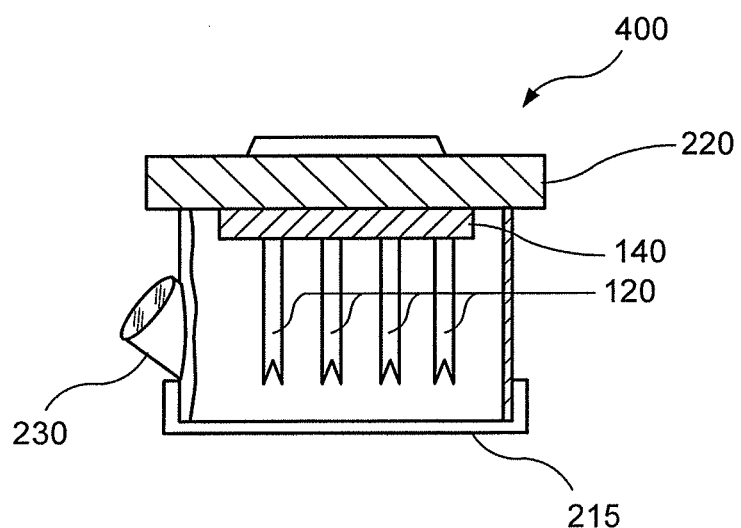
F I G. 4

APPARATUS AND METHOD FOR TISSUE BIOPSY

CROSS REFERENCE TO RELATED APPLICATION

The present application relates to and claims priority from International Patent Application No. PCT/US2012/022980 filed Jan. 27, 2012, and from U.S. Provisional Patent Application Ser. No. 61/437,493 filed Jan. 28, 2011, the disclosures of which are incorporated herein by reference in their entireties.

TECHNICAL FIELD

The present invention relates to methods and apparatus for obtaining biological tissue samples, e.g., for biopsies or the like.

BACKGROUND INFORMATION

A punch biopsy is a procedure that removes a sample of skin or other tissue, which can be used for external analysis and/or detection of any of a variety of conditions within the tissue. A punch biopsy can be used, e.g., for the diagnosis of squamous cell carcinoma and melanomas. Punch biopsies can generally include a removal of a relatively large tissue sample using, for example, a round shaped knife or tube typically having a diameter of about 2 mm or greater, up to about 4-6 mm. The underlying portion of the sample may be cut using a scalpel or the like, and the tissue sample removed from the patient using small forceps or surgical tweezers. The tissue sample can then be placed in a fixative or the like to stabilize the sample and sent to a lab for analysis.

For example, a skin punch biopsy tissue sample can generally include a full thickness of skin from the surface down to the underlying subcutaneous fat. These relatively large tissue samples are often preferred to facilitate the handling of the samples for analysis and identification of their orientation after removal from the patient. However, conventionally, the removal of such large tissue samples may require an extended healing time and/or stitches, and can further leave markings after healing has occurred.

Accordingly, there may be a need to provide a simpler and more reliable method and apparatus which can overcome at least some of such exemplary deficiencies, and which can obtain punch biopsy samples safely, e.g., without requiring special skills or facilities, and that addresses the limitations described above.

SUMMARY OF EXEMPLARY EMBODIMENTS

The herein described exemplary embodiments of the present invention pertain to a method and apparatus. Synergetic effects may arise from different combinations of the features and embodiments described herein, although all such combinations might not be described in detail. Further, it shall be noted that embodiments of the present invention concerning a method might be carried out with the order of the steps as described, nevertheless this need not be the only or essential order of the steps of the method unless otherwise specified.

Exemplary embodiments of the present invention relate to simple, inexpensive, and safe methods, apparatus and devices for a removal of one or more tissue samples that can be smaller than certain samples that can be removed in conventional punch biopsy procedures, such that the removal of such small tissue samples is well-tolerated, for example, the removal sites may heal quickly without significant bleeding or risk of infection, and that may not require stitches. The small tissue samples can be easily handled (e.g., sent to a lab for analysis) more easily analyzed, and can facilitate a more precise spatial identification of portions of the removed sample.

Exemplary embodiments of the present invention can be directed to an apparatus that includes one or more hollow needles, which are adapted and/or structured to be inserted into a biological tissue to obtain tissue samples therefrom. An exemplary hollow needle can be provided with a tapered or pointed distal end configured or structured to be inserted into the tissue, and the needle can be adapted or structured to remove a core sample of the tissue in a hollow portion of the needle when the needle is subsequently withdrawn from the biological tissue. For example, the internal diameter of the hollow needle can be less than about 2 mm, e.g., about 1 mm, or less than about 1 mm. In certain exemplary embodiments, the internal diameter of the needle can be about 0.5 mm or less. The needles can be formed using metal tubes having a gauge that is greater than 16 gauge in size, e.g., between about 21 and 25 gauge. Other diameters can be used according to certain further exemplary embodiments of the present invention. A length of the needle can be between about 1 mm and 5 mm, or longer needle lengths can be used in further embodiments.

The exemplary hollow needle can optionally be provided with one or more openings or windows provided on the wall thereof. Such openings can facilitate access to the tissue sample without removing the sample from the needle. A plurality of markings can optionally be provided along at least a portion of the length of the needle, e.g., proximal to the one or more openings, to facilitate an identification of distances along the tissue sample in the needle.

The one or more exemplary hollow needles can be affixed or coupled to a handle or substrate to facilitate grasping and manipulation of the needle and/or to provide mechanical stability to the needle. The handle or substrate can be adjustably coupled to the one or more hollow needles, e.g., using a friction fitting, a clamp, a threaded arrangement, or the like. Such adjustable coupling can be adapted to vary the protrusion length of one or more of the hollow needles beyond a lower surface of the handle or substrate, e.g., to vary the effective needle length or maximum penetration distance when the apparatus is pressed into a tissue region. The coupling of the needles to the substrate can be adapted such that lengths of the needles can be adjusted either individually or as a group. Such adjustment can be performed using one or more threaded or screw arrangements, clamps or friction fittings, or the like.

The exemplary apparatus can include a plurality of needles, e.g., between about 2 and 12 needles, or up to 25 needles, or up to about 100 needles or more. The needles can be coupled to a substrate having a shape that is substantially square or round, rectangular, ovoid, triangular, or another shape. A width of the substrate (e.g., a diameter of a round substrate or side length of a square, triangular or rectangular substrate) can be between about 3 mm and about 30 mm. Spacings between needles on the substrate can be between about 1 mm and about 20 mm. The spacings between needles can be substantially uniform, or they can vary over the substrate. In further embodiments of the invention, the needles can be affixed or attached to an actuating arrangement, if provided. The geometrical characteristics of the actuating arrangement and arrangement of the needles thereon can include any of these shapes and spacing characteristics.

The needle can be formed of a metal or metal alloy, e.g., a surgical steel, a polymer or plastic, an epoxy, a resin, a glass, or another structural material. In certain embodiments, the needle can be formed using a plurality of materials, such as a metal or metal alloy or another hard material for the distal end that includes a cutting surface, and a polymer or plastic, an epoxy, a resin, a glass, or another structural material for at least a portion of the needle shaft.

According to further exemplary embodiments of the present invention, a tissue-sampling apparatus can be provided that can include one or more of the hollow needles as described herein that is provided within an enclosure and optionally coupled to a substrate. An actuating mechanism can be provided to extend the one or more needles into the tissue to be sampled when activated, and/or to retract the one or more needles from the tissue. The actuating mechanism can include a spring-loaded device, a piston, a plunger, and/or the like. The actuating mechanism can be adjustable to control a penetration depth of the one or more needles into the tissue when the exemplary apparatus is placed on or near the surface of the tissue. Different ones of the needles can have different penetration lengths, for example, the position of one or more of the needles can be adjustable with respect to the substrate and/or actuating mechanism.

The exemplary apparatus can be further provided with a positioning arrangement configured to facilitate viewing of the surface of the tissue beneath the apparatus, and a precise placement of the one or more needles such that they penetrate the tissue at or proximal to one or more predetermined locations. The positioning arrangement can include one or more optical elements, such as a mirror or reflector, a prism, or a lens, and may also include an illuminating arrangement adapted to direct light onto the tissue when the apparatus is being used.

In further exemplary embodiments of the present disclosure, the apparatus can be adapted or structured to facilitate fixing at least a portion of the one or more needles in an embedding medium after tissue samples have been obtained in the needles. For example, the enclosure, if provided, can be structured to serve as a mold for a embedding medium. In further embodiments, the substrate or handle can be adapted to attach to such mold and optionally form a portion thereof. The embedding medium can include any conventional medium such as, e.g., a wax or paraffin, agar, gelatin, a plastic, a polymer, an acrylic, or an epoxy or epoxy resin. At least a portion of the needle can be formed using a material that can be easily cut or ground, such as a plastic, a polymer, an acrylic, or an epoxy, for example, when the needle is fixed in a embedding medium.

These and other objects, features and advantages of the present invention will become apparent upon reading the following detailed description of exemplary embodiments of the present invention, when taken in conjunction with the appended drawings and claims.

BRIEF DESCRIPTION OF THE DRAWINGS

Further objects, features and advantages of the present invention will become apparent from the following detailed description taken in conjunction with the accompanying figures showing illustrative examples, results and/or features of the exemplary embodiments of the present invention, in which:

FIG. 3 is a schematic side view of a tissue-sampling apparatus in accordance with yet further exemplary embodiments of the present invention; and FIG. 4 is a schematic side view of the tissue-sampling apparatus in accordance with still further exemplary embodiments of the present invention.

Figure 1:
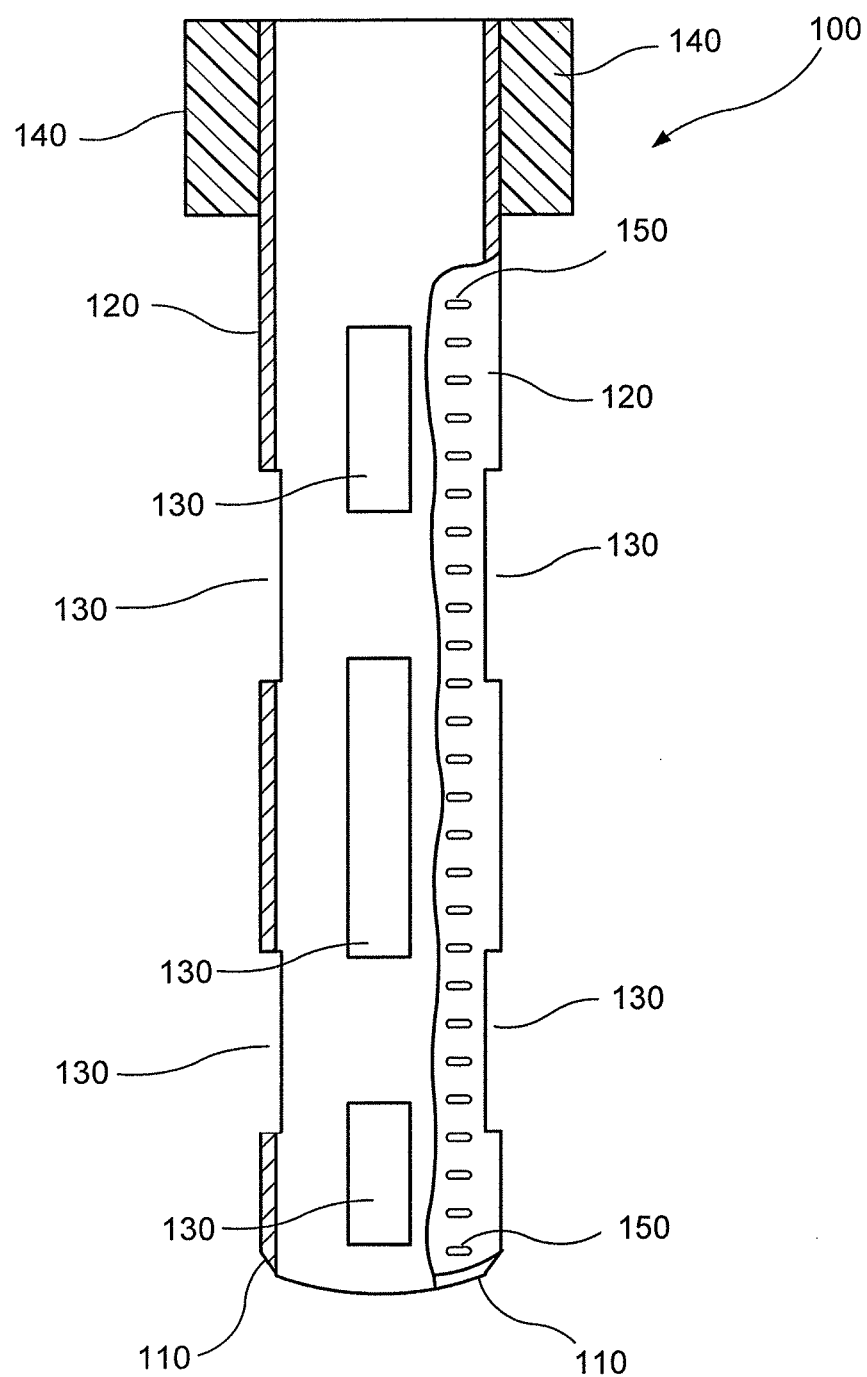
FIG. 1 is a schematic side view of a tissue-sampling apparatus in accordance with exemplary embodiments of the present invention.

Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present invention as defined by the appended claims.

DETAILED DESCRIPTION OF EXEMPLARY EMBODIMENTS

Exemplary embodiments of the present invention are directed to exemplary methods, devices, and apparatus for reliably removing small tissue samples in a punch biopsy procedure. For example, a cross-sectional view of an exemplary apparatus 100 for removing a tissue sample according to a first exemplary embodiment of the present invention is shown in FIG. 1. The exemplary apparatus 100 of FIG. 1 can include a hollow needle 120 that is configured or structured to be inserted into a region of tissue to be analyzed, and to remove a portion of such tissue when the needle 120 is withdrawn from the tissue. The internal diameter of the exemplary needle 120, or diameter of the lumen, can be less than about 2 mm to reduce scarring or other skin markings, excessive bleeding, etc., after the tissue sample is removed from the surrounding tissue. Smaller diameters can also facilitate the removal of the tissue sample from the surrounding the biological tissue. For example, the internal diameter of the needle 120 can be about 1 mm or less than 1 mm. In certain embodiments, the internal diameter can be about 0.5 mm or less. In terms of conventional needle gauge sizes, the needle size can be greater than 16 gauge, or preferably between about 21 and 25 gauge. The tissue samples removed by needles 120 having such diameters can be better tolerated than larger tissue samples removed by conventional biopsy needles, which typically have diameters of about 2-4 mm or greater. Larger or smaller diameters can also be used in accordance with certain exemplary embodiments of the present invention.

Walls of the exemplary needle 120 can be optionally be provided with one or more windows, holes, or openings 130 therethrough, as illustrated in FIG. 1. The openings 130 shown in FIG. 1 are optional, and are not required in all embodiments of the present invention. According to certain exemplary embodiments of the present disclosure, the openings 130, if present, can be substantially rectangular in shape, as shown in FIG. 1, or they can have another shape such as oval shapes, square shapes, etc. Such openings 130 can be provided at a plurality of locations around the circumference of the needle 120. For example, the openings 130 can be staggered and/or offset such that the ends of adjacent openings 130 overlap for a particular and/or predetermined distance. This exemplary configuration can provide at least one opening through a portion of the wall of the needle 120 at substantially every longitudinal distance along the axis along which the needle 120 extends. The openings 130 can facilitate access to and/or analysis of portions of the tissue sample that may be present in the needle 120. For example, the openings 130 can facilitate a direct visual observation of the tissue sample. The openings 130 can also facilitate a direct access to portions of the tissue sample held within the needle 120 for subsequent removal and/or analysis of small portions of the tissue sample.

In yet further exemplary embodiments of the present invention, the exemplary apparatus 100 can optionally include a plurality of calibrated markings 150 spaced along the longitudinal direction of the needle 120. Such markings 150 can facilitate an identification of distances and/or depths in the tissue sample that can be observed through the openings 130. The markings 150 can also facilitate placement of the handle or substrate 140 at a particular location to provide a predetermined protrusion length of the needle 120 beyond the distal end of the handle or substrate 140, in exemplary embodiments where the position of the handle or substrate 140 relative to the needle 120 is adjustable.

The exemplary apparatus 100 can optionally include a handle or substrate 140 provided at a proximal portion of the needle 120. The handle or substrate 140 can facilitate holding and manipulation of the needle 120, e.g., by a user, and can be provided in various sizes and shapes. The handle or substrate 140 can also be removable from the needle 120 after the tissue sample has been obtained. Further, a distal end of the handle can be wider than the outside diameter of the needle 120, as shown in FIG. 1. Accordingly, a position of the handle or substrate 140 on the shaft of the needle 120 can control the penetration depth of the needle 120 when the apparatus 100 is inserted into tissue to obtain a tissue sample. The apparatus 100 can be inserted into the tissue until a bottom portion or distal surface of the handle or substrate 140 contacts the tissue surface, and then be withdrawn to obtain a tissue sample having a predetermined depth. For example, the apparatus 100 can be provided with a handle or substrate 140 such that the protrusion length of the needle 120 beyond the distal end of the handle or substrate 140 is a predetermined distance.

In a further exemplary embodiment, the position of the handle or substrate 140 relative to the needle 120 can be adjustable. The handle or substrate 140 can be affixed to the needle 120 using, e.g., a friction fit, a conventional threaded coupling, a clamping mechanism, or the like. Such an adjustable arrangement can be used, for example, to vary or alter the length of the needle 120 projecting below the handle or substrate 140 for particular uses, e.g., to sample specific tissue structures or to obtain tissue samples down to a predetermined depth below the tissue surface. For example, a penetration depth of the needle 120 when the apparatus 100 is inserted into tissue to be sampled can be varied by varying the projection length. In further embodiments, a plurality of handles 140 having different lengths can be provided and affixed to a needle 120 having a particular size, where the choice of handle size can determine the protrusion length of the needle 120 beyond the distal end of the particular handle or substrate 140.

The length of the needle 120 protruding from the lower portion of the handle or substrate 140 can generally be, e.g., between about 1 mm and about 5 mm. This exemplary effective length of the needle 120 can be determined based on the intended use. For example, a shorter needle 120 having a length between about 1 and 3 mm can be used to obtain tissue samples from the epidermis or near the surface of skin tissue. Longer needle lengths can be provided to obtain tissue samples from structures located deeper below the surface of the tissue. For example, longer protrusion lengths can be provided in the exemplary apparatus 100, e.g., lengths greater than 5 mm. Tissue samples relatively close to the surface can be obtained with such longer needles 120 by inserting only a portion of the needle 120 into the tissue being sampled and then withdrawing it. An insertion depth can be determined, e.g., using the markings 150 and/or positions of the windows 130, if such optional features are provided on the apparatus 100.

A distal end 110 of the needle 120 can be sharpened and/or otherwise configured/structured to facilitate (i) a penetration of the needle 120 into the region of interest of the tissue, and (ii) a separation of the tissue sample from the surrounding tissue. For example, the distal end 110 of the needle 120 can be provided with a sharpened or tapered edge. According to certain exemplary embodiments, the distal end 110 of the needle 120 can be provided with a plurality of sharp points to facilitate an insertion of the needle 120 into the biological tissue and/or removal of the tissue sample when the needle 120 is withdrawn.

In an exemplary operation, the tissue region to be examined can be numbed, cooled, and/or partially or completely frozen using conventional procedures. The exemplary apparatus 100 can then be inserted into this tissue region, such that the distal end 110 of the needle 120 penetrates the tissue to a desired depth. In certain exemplary embodiments, this depth can correspond to a protrusion distance of the needle 120 beyond the distal end of the handle or substrate 140, as described herein. Alternatively, the insertion depth can be determined using the markings 150 and/or window locations 130, if either is present, as a guide.

The exemplary apparatus 100 can then be removed from the tissue such that the sample of the tissue to be analyzed is retained within the hollow needle 120. The exemplary apparatus 120 can be twisted slightly around the longitudinal axis thereof to facilitate an insertion into the tissue and/or the separation of the tissue sample from the surrounding tissue. The tissue sample can be held within the hollow center of the needle 120. Accordingly, the needle 120 can facilitate the protection and/or stabilization of the tissue sample enclosed therein, and can also maintain a known orientation of the tissue sample based on the direction in which the needle 120 was inserted into the surrounding tissue.

The tissue region to be sampled can be on or near the skin surface, in which case the tissue sample can be removed by inserting the exemplary apparatus 100 directly through the skin surface and then removing it. Biopsy samples from tissue regions located deeper within the body can be obtained by first providing an incision to access the tissue region, then inserting the exemplary apparatus 100 into this deeper tissue, and removing it to obtain the tissue sample.

According to one exemplary procedure according to the present invention, the exemplary apparatus 100 can be inserted into a region of the tissue to be analyzed, optionally twisted or rotated to facilitate insertion and/or separation of a tissue sample from the surrounding tissue, and then removed from the tissue such that a small tissue sample is retained within the distal portion of the needle 120. Such samples having a small diameter can be more easily separated from the surrounding tissue than the larger tissue samples, which have a larger area beneath them that can still remain attached to underlying tissue after the sides of the tissue sample are cut or separated. The depth of the tissue sample thus obtained can be easily selected and monitored using the markings 150 provided on the needle 120.

After the exemplary apparatus 100 is removed from the region of tissue, the needle 120 that includes the tissue sample therein can be placed in a small vial or sleeve that can include formaldehyde or another solution or liquid that can preserve and stabilize the tissue sample. The handle or substrate 140, if provided, can also be removed prior to placing the needle 120 into the vial. For example, the handle or substrate 140 can be attached to the needle 120 using a spring-loaded latch or the like. The apparatus 100 can be manipulated by holding the handle or substrate 140, and the needle 120 can then be released from the handle 120 and dropped into the vial without being handled directly. After the needle 120 containing the tissue sample is placed in the vial, the vial can be sealed and sent to a laboratory or other facility for analysis.

Figure 2:
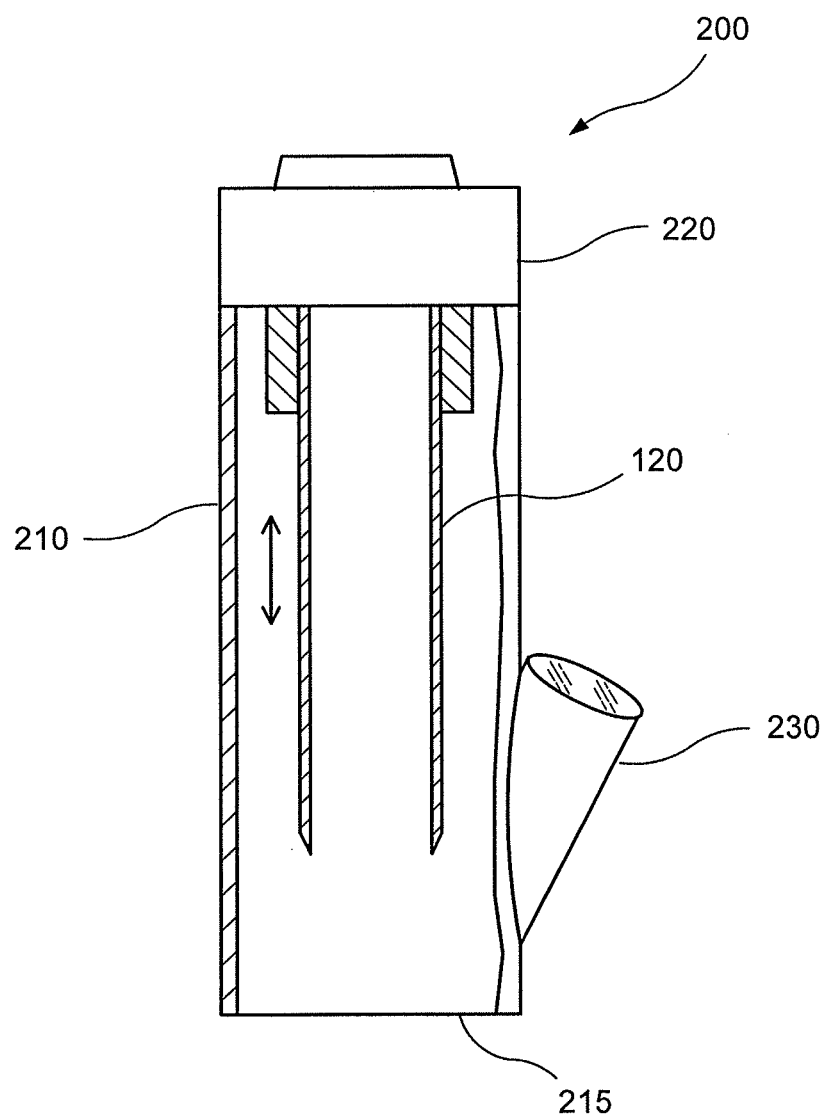
FIG. 2 is a schematic side view of the tissue-sampling apparatus in accordance with further exemplary embodiments of the present invention.

According to another exemplary embodiment of the present invention, an exemplary apparatus 200, illustrated in FIG. 2, can be provided that includes the needle 120 according to any of the various embodiments described herein, and a housing or enclosure 210. The enclosure 210 can be mechanically coupled to the needle 120, e.g., to facilitate a manipulation of the needle 120 and an insertion of the needle 120 into the tissue to be sampled. The enclosure 210 can include an actuating mechanism 220 configured to insert the needle 120 into the tissue to be sampled, e.g., when a lower portion of the enclosure 210 is placed in contact with the surface of the tissue region.

For example, the actuating mechanism 220 can include a spring-loaded actuator or the like that can be configured or structured to extend the distal portion of the needle 120 into the tissue when activated. In a further exemplary embodiment of the present invention, the actuating mechanism 220 can include a plunger, piston, or the like. The actuating mechanism 220 can be manually activated, e.g., by applying a force to the plunger or piston, or to a trigger or switch coupled to the actuating mechanism 220. The needle 120 can be affixed or coupled directly to the actuating mechanism 220. In further embodiments, the needle 120 can be affixed directly to a substrate 140 (not shown in FIG. 2), and the substrate 140 can be further coupled to the actuating mechanism 220.

The protrusion distance of the needle 120 beyond the lower surface of the enclosure 210 can be predetermined and optionally adjustable, such that the needle 120 penetrates a known distance into the tissue when the exemplary apparatus 200 is placed on the surface of the region of the tissue to be sampled and the actuating mechanism 220 is subsequently activated. For example, a threaded arrangement can be provided to affix or mechanically couple the needle 120 to the actuating mechanism 220 and/or to a first portion of the enclosure 210, such that the protrusion distance of the needle 120 can be adjusted by twisting the actuating mechanism 220 and/or the first portion of the enclosure 120 relative to a second portion of the enclosure. In further exemplary embodiments, the actuating mechanism 220 can include a plurality of stops that are configured to control the protrusion distance of the needle 120 beyond the lower portion of the enclosure 210, for example, when the actuating mechanism 220 is activated.

One or more markers can optionally be provided on the enclosure 210, the needle 120, and/or the actuating mechanism 220 in any of the exemplary embodiments described herein to facilitate the adjustment and/or control of the protrusion length of the needle 120 when the actuating mechanism 220 is activated.

In further exemplary embodiments, the actuating mechanism 220 can be adapted, configured and/or structured to retract the needle 120 back into the enclosure 210 after the needle 120 has been inserted into the tissue to be sampled. The distal end of the enclosure 210 can optionally be provided with a covering arrangement 215. The covering arrangement 215 can be, for example, a film, e.g., a sheet of foil, plastic, or another thin material that the needle 120 can easily penetrate when the needle 120 is advanced so it protrudes from the housing 210, e.g., when the actuating mechanism 220 is activated. In certain exemplary embodiments, the optional covering arrangement 215 can be a solid cap, a plug, or a stopper that is either fixed in place (e.g., adhered to the housing 210 or formed as a part thereof) or removable (e.g., affixed to the distal end of the enclosure 210 with screw threads, a frictional fitting, or the like). The covering arrangement 215 can be adapted to cover the retracted needle 120 within the enclosure 210, to secure the needle 120 within the enclosure 210, to seal the interior volume of the enclosure 210, to protect the tissue sample within the needle 120 from contamination, etc. The covering arrangement 215 can optionally be provided with a hole aligned with the needle 120 and located such that the needle 120 can pass through the hole when the needle is extended, e.g., when the actuating mechanism 220 is activated.

According to certain further exemplary embodiments of the present invention, a fluid can be provided in the enclosure 210 after the needle 120 containing a tissue sample is retracted. Such fluid can include a biological preservative or the like configured to preserve and/or prevent deterioration or degradation of the tissue sample. For example, the fluid can be provided in a vial (not shown) that is affixed to the enclosure 210 or in fluid communication with the interior volume of the enclosure 210. In still further exemplary embodiments, the actuating mechanism 220 can be configured and/or structured to eject the needle 120 containing the tissue sample into a vial containing such fluid or another such container, to facilitate preservation and transportation of the tissue sample, e.g., prior to analysis of the tissue sample in a remote facility.

According to another exemplary embodiment of the present invention, an optional positioning arrangement 230 can be provided on or proximal to the enclosure 210. The positioning arrangement 230 can facilitate a deployment of the needle 120 into a particular location of the tissue when the actuating mechanism 220 is activated. For example, the location where the tissue sample is to be obtained can be marked on the tissue surface by the user or practitioner using any conventional tissue marking technique. The positioning arrangement 230 can then be used to align the exemplary apparatus 200 with the tissue surface such that the needle 120 can enter the tissue at the marked location when the apparatus 200 is activated to propel the needle 120 into the tissue. Although the apparatus 200 is shown with such positioning arrangement 230 in FIG. 2, the apparatus 200 can be provided and used without such positioning arrangement 230.

The exemplary positioning arrangement 230 can include one or more optical elements affixed to and/or formed as part of the enclosure 210. For example, the positioning arrangement 230 can include one or more lenses configured to facilitate the viewing of a portion of the surface of the tissue beneath the apparatus 200 when the apparatus 200 is placed on the surface of the tissue. The positioning arrangement 230 can further include one or more reflecting surfaces to facilitate such viewing of the surface of the tissue from different angles and/or positions. A set of crosshairs or the like can be provided in the positioning arrangement 230 to identify the precise location where the needle 120 will enter the tissue when the actuating mechanism 220 is activated.

In additional exemplary embodiments of the present invention, the positioning arrangement 230 can further include an illumination source to facilitate the viewing of the surface of the tissue beneath the apparatus 200. In some exemplary embodiments, at least a portion of the enclosure 210, e.g., a portion proximal to the distal end thereof, is formed using a transparent or translucent material to facilitate such viewing and/or to allow ambient light to illuminate the tissue surface beneath the distal end of the apparatus 200. The positioning arrangement 230 or a portion thereof can be provided as an assembly separate from the housing 210, e.g., an illumination source and/or one or more lenses or reflectors, which can be reused with a plurality of housings 210 and needles 120. The positioning arrangement 230 or a portion thereof can optionally be formed as part of the housing 210 or permanently affixed thereto.

In yet another exemplary embodiment of the invention, an apparatus 300 can be provided as shown in FIG. 3. The exemplary apparatus 300 includes a plurality of needles 120 affixed to or coupled to a common handle or substrate 140. The needles 120 can be provided with some or all of the features of the needle 120 shown in FIG. 1 and described herein such as, e.g., windows 130 and/or markings 150, etc. The needles 120 of the exemplary apparatus 300 shown in FIG. 3 can all have the same size, or certain ones may have different diameters and/or different protrusion distances from the bottom surface of the base 140.

In yet further embodiments, some of the needles 120 can be adjustably attached or affixed to the base 140, e.g., by a threaded coupling or screw arrangement, a friction fitting, a clamp, or the like as described above, which can facilitate variation of the protrusion length of the needles 120 below the lower surface of the base 140. The protrusion length of individual needles 120 can be separately adjustable, or this length may be adjustable simultaneously for all needles 120 in the apparatus 300. For example, at least two of the needles 120 in the exemplary apparatus 300 can have different protrusion lengths.

The apparatus 300 can include any number of needles 120, for example, between about 2 and 12 needles 120. Larger numbers of needles 120 can also be used in certain embodiments, e.g., between 2 and about 25 needles 120, or between 2 and about 100 needles 120. The number of needles 120 provided in the apparatus 300 can be determined based on the intended use. For example, if tissue samples are desired from a small structure such as a typical pigmented lesion or carcinoma, or a biological structure of indeterminate shape or inexact location, a smaller number of the needles 120, e.g., between about 2 and 12 needles 120, can be provided in the exemplary apparatus 300 to ensure that a portion of the structure would be present in at least one tissue sample removed by the needles 120. If it is desirable to determine a spatial variation in tissue characteristics or to obtain tissue samples from a diffuse structure such as, for example, from a lentigo maligna melanoma, an angioscarcoma, or a desmoplastic tumor, a larger number of the needles 120 can be provided to obtain more tissue samples when the exemplary apparatus 300 is applied to a target area of tissue. The apparatus 300 can include more than 12 needles 120 for certain uses, for example, up to about 30 needles 120, to obtain tissue samples from moderate-sized structures and/or provide a more detailed spatial sampling of the structure, or even up to about 100 needles 120. The apparatus 300 can be adapted such that the plurality of needles 120 are inserted substantially simultaneously into the biological tissue and/or simultaneously withdrawn therefrom.

The spacing and/or separation distance between the needles 120 in the exemplary apparatus 300 can be between about 1 mm and about 20 mm. The exemplary apparatus 300 having smaller separation distances between the needles 120 can be used, e.g., to obtain a plurality of tissue samples from a particular target area or a small biological structure. Larger separation distances can be provided to obtain tissue samples over a larger target area or from different portions of a larger biological structure. Needle separation distances greater than about 20 mm can also be provided in further exemplary embodiments of the present invention, e.g., for obtaining tissue samples over a very large target area or from a large biological structure, or to obtain a higher spatial density of tissue samples from a particular biological feature or portion thereof.

The width of the substrate 140, which can correspond to e.g., a side length or diameter for a substantially square or circular substrate 140, respectively, can be between about 3 mm and about 30 mm. Other substrate shapes can be provided in further exemplary embodiments of the invention such as, e.g., rectangular, ovoid, triangular, or the like. The exemplary shape of the substrate can be determined at least in part by characteristics of the target region of tissue and/or the biological structure from which tissue samples are to be taken from. A plurality of needles 120 can be provided in any one of various spacings or patterns over the substrate 120. For example, the needles 120 can be arranged in a regular square or triangular array. In other embodiments, the needles 120 can be spaced closer together in one portion of the substrate 140 than in another portion thereof, e.g., a non-uniform density of needles 120 can be provided. An apparatus 300 having such non-uniformity can be used, e.g., to obtain more tissue samples from a particular identified biological structure and fewer samples from proximal areas of tissue.

In further embodiments, one or more of the needles 120 in the exemplary apparatus 300 can be provided with one or more identifying characteristics, such as a distinct coloration, marking, shape, size or diameter, or the like. Such identifying characteristics can be used to assess the orientation of the needles 120 and tissue samples or portions contained therein, e.g., after the exemplary apparatus 300 is withdrawn from the tissue. The target region of tissue can optionally be labeled with one or more identifying markings. Such markings can facilitate identification of the orientation and/or location of the plurality of needles 120 and tissue samples they may contain, relative to the target region of tissue. The relative location of the tissue portions within the target region can be determined based on the relative locations of the needles 120 in the apparatus 300.

FIG. 4 illustrates an exemplary apparatus 400 according to further embodiments of the invention. The apparatus 400 is substantially similar to the exemplary apparatus 200 shown in FIG. 2, and also provides a housing or enclosure 210. The exemplary apparatus 400 includes a plurality of the needles 120. The enclosure 210 can be mechanically coupled to the needles 120, e.g., to facilitate a manipulation of the needles 120 and/or insertion of the needles 120 into the tissue to be sampled.

The enclosure 210 can optionally include an actuating mechanism 220 configured to insert the needles 120 into the tissue to be sampled. The needles 120 can be coupled or affixed directly to the actuating mechanism 220, or they can be coupled or affixed directly to the handle or substrate 140, which can be further coupled to the actuating mechanism 220. The actuating mechanism 220 in the exemplary apparatus 400 can include any of the features that were described herein above with respect to the apparatus 200 shown in FIG. 2. For example, the actuating mechanism 220 shown in FIG. 4 can include the spring-loaded actuator or the like, the plunger or piston, and/or it can optionally be manually activated. The actuating mechanism 220 can be adapted such that the plurality of needles 120 are inserted substantially simultaneously into the biological tissue and/or simultaneously withdrawn therefrom.

The protrusion distances of the needles 120 beyond the lower surface of the enclosure 210 can be predetermined and optionally adjustable, such that the needles 120 penetrates a known distance into the tissue when the exemplary apparatus 400 is placed on the surface of the region of the tissue to be sampled and the actuating mechanism 220 is subsequently activated. Each of the needles 120 can be individually adjustable, and/or all of the needles 120 in the exemplary apparatus 400 can be adjustable simultaneously, using the exemplary arrangements and mechanisms described above with respect to the exemplary apparatus 200. In further exemplary embodiments, the exemplary apparatus 400 can be adapted, configured, and/or structured to retract the needles 120 back into the enclosure 210, similar to that described for the exemplary apparatus 200 herein.

The distal end of the enclosure 210 in the exemplary apparatus 400 can optionally be provided with the covering arrangement 215, e.g., a sheet of foil, plastic, or another thin material that the needles 120 can penetrate when they are advanced to protrude from the housing 210. In certain exemplary embodiments, the optional covering arrangement 215 can be a solid cap, plug or stopper that is removable (e.g., affixed to the distal end of the enclosure 210 with screw threads, a frictional fitting, or the like). The covering arrangement 215 can further be configured or structured to be placed over the distal end of the enclosure 210, e.g., to cover the retracted needles 120 within the enclosure 210, to secure the needles 120 within the enclosure 210, to seal the interior volume of the enclosure 210, to protect the tissue samples in the needles 120 from contamination, etc. The covering arrangement 215 can optionally include a plurality of small holes therethrough, e.g., where the diameter of the holes may be substantially the same as or slightly larger than the outside diameter of the corresponding needles 120. The holes can be located in the exemplary covering arrangement 215 such that the needles 120 can pass through the holes when the needles 120 are advanced and project from the enclosure 210, e.g., when the actuating mechanism 220 is activated.

The exemplary apparatus 400 can optionally include other features that are similar to or the same as those described for the exemplary apparatus 200 shown in FIG. 2 or the exemplary apparatus 300 shown in FIG. 3, or combinations of such features, such as a fluid provided in the enclosure 210, the actuating mechanism 220 being configured or adapted to eject the needle 120 into a vial or other container, an optional positioning arrangement 230, a size of the substrate 140, lengths, diameters, spacings, and arrangements of the plurality of needles 120, etc. For example, a positioning arrangement 230, if provided on the apparatus 400, can include any of the features described above with respect to the positioning arrangement 230 of the apparatus 200.

In any of the exemplary embodiments described herein and/or illustrated in FIGS. 1-4, the needle 120 can be formed of one or more materials appropriate for a particular application or use. For example, the needle 120 can be formed of a surgical steel or other metal or metal alloy, such as those used to form conventional hypodermic needles or biopsy punches. In certain embodiments, the distal portion of the needle 120 including, e.g., the cutting edge, can be formed using such metals or metal alloys, and the needle shaft or a portion thereof can be formed of a different material. For example, the needle shaft can be formed using an acrylic or plastic, or a polymer such as polyethylene, nylon, or the like. For example, an optically transparent material can be used to facilitate observation and/or analysis of the tissue sample contained in the needle. A proximal portion of the needle 120 can also be formed of a material such as a metal or metal alloy, or another structural material that can be sufficiently strong to provide mechanical strength and stability, e.g., if the needle 120 is attached to the handle or substrate 140 or to the activation arrangement 220.

In further exemplary embodiments, the one or more needles 120 can be adapted to be fixed in an appropriate medium after tissue samples have been collected therein. The substrate 140 and/or enclosure 210, if provided, can be configured to facilitate such fixing, e.g., by providing a mold body or being adapted to attach to a mold. A embedding medium such as a paraffin or other wax, an acrylic, an epoxy, a resin, or a curable polymer, or any other conventional embedding medium can be used. Sectioning of the one or more needles 120 in the embedding medium can then be performed, e.g., using conventional sectioning techniques and devices. In further embodiments, at least a portion of the needle 120 can be formed using a material that is easily cut or abraded using conventional sectioning devices and systems. For example, at least a portion of the needle 120 can be formed using the same or a substantially similar material as a embedding medium that the needles 120 are fixed in. The needles 120 can be used to obtain and support tissue samples having small widths, and fixing the needles 120 in a medium and then sectioning and/or grinding them can provide accurate spatial identification of portions of the tissue samples during subsequent analysis.

The exemplary method and apparatus described herein can facilitate removal and stabilization of a small tissue sample using a small needle, and the handling and transfer of the small sample to an apparatus or remote facility for analysis. The exemplary apparatus 100/200/300/400 can also facilitate observation of, and access to, portions of the sample that are at a known depth and orientation relative to the surrounding tissue from which it was removed. The present invention thereby facilitates biopsy samples to be obtained and analyzed, where the tissue samples are smaller than those used in conventional biopsy procedures. The use of such smaller tissue samples can facilitate healing and avoid the removal of excess tissue and/or formation of scars or markings resulting from such removal.

The foregoing merely illustrates the principles of the invention. Other variations to the disclosed exemplary embodiments can be understood and effected by those skilled in the art in practising the claimed invention from a study of the drawings, the disclosure, and the appended claims. In the claims, the word "comprising" does not exclude other elements or steps and the indefinite article "a" or "an" does not exclude a plurality. The mere fact that certain measures are recited in mutually different dependent claims does not indicate that a combination of these measures cannot be used advantageously. Any reference signs in the claims should not be construed as limiting the scope of the claims. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the present invention.

What is claimed is:

1. A method for obtaining at least one portion of a biological tissue for analysis, comprising:
    at least partially inserting at least one hollow needle having a distal end at least partially into the biological tissue, the hollow needle including a central lumen and at least one opening on a wall thereof;
    withdrawing the at least one needle from the biological tissue to extract the at least one portion of tissue, wherein the distal end of the at least one hollow needle is adapted and/or structured to facilitate extraction of the at least one portion from the tissue within the central lumen when the needle is withdrawn therefrom, and wherein a diameter of the lumen is less than about 2 mm;
    positioning the at least one needle and the at least one portion of tissue retained in the at least one needle in a liquid for laboratory analysis, the at least one opening on the wall of the at least one hollow needle being adapted or structured to facilitate access of the liquid to the tissue portion while the tissue portion is retained within the central lumen; and
    performing laboratory analysis on the tissue portion while the tissue portion is retained in the at least one needle.

2. The method of claim 1, wherein the diameter of the lumen is less than about 1 mm.

3. The method of claim 1, wherein the at least one hollow needle is a plurality of needles, and wherein the plurality of needles are inserted substantially simultaneously into the biological tissue.

4. The method of claim 1, further comprising fixing at least a portion of the at least one needle in an embedding medium after withdrawing the at least one needle from the biological tissue.

5. The apparatus of claim 1, wherein the at least one hollow needle is formed from one of an optically transparent or translucent material.

6. The apparatus of claim 5, wherein the at least one hollow needle is formed of one of an acrylic, a plastic, glass, or a polymer.

7. The method of claim 1, wherein the positioning of the at least one needle and the at least one portion of tissue retained in the at least one needle in the liquid for laboratory analysis is achieved without directly handling the needle.

8. The method of claim 1, further comprising releasing the at least one needle from a handle and dropping the at least one needle into a vial.

* * * * *